US00PP37798P2

(12) United States Plant Patent
Bean et al.

(10) Patent No.: US PP37,798 P2
(45) Date of Patent: Oct. 20, 2026

(54) ***AGAPANTHUS* PLANT NAMED 'DWAGHYB21'**

(50) Latin Name: ***Agapanthus* hybrid**
Varietal Denomination: DWAgHyb21

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 19/565,486

(22) Filed: Mar. 12, 2026

(30) Foreign Application Priority Data

Jul. 18, 2025 (QZ) ..... PBR 20251595

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
CPC ..... A01H 5/02; A01H 5/00; A01H 6/04
See application file for complete search history.

(56) References Cited

U.S. PATENT DOCUMENTS

PP26,336 P2 * 1/2016 Bean ..... A01H 6/04
Plt./398

* cited by examiner

*Primary Examiner* — June Hwu
(74) *Attorney, Agent, or Firm* — Penny J. Aguirre

(57) ABSTRACT

A new cultivar of *Agapanthus* plant named 'DWAgHyb21' that is characterized by its long flowering period with re-blooming, its flowers that are deep purple-blue in color and open from flower buds that are dark purple-blue in color, its very compact plant habit with suitability for use in small containers, its very floriferous blooming habit with a high number of flowering stems, and its high resistance to crown and root rot.

3 Drawing Sheets

Botanical classification: *Agapanthus* hybrid.
Varietal denomination: 'DWAgHyb21'.

CROSS REFERENCE TO RELATED APPLICATIONS

This application claims priority to European Community Plant Variety Office (CPVO) Plant Breeder's Rights Application No. 2025/1595 filed Jul. 18, 2025. The Applicant received the information for the Plant breeders' rights application directly from the Inventor.

BACKGROUND OF THE INVENTION

The present invention relates to a new and distinct cultivar of *Agapanthus* of hybrid origin and will be referred to hereafter by its cultivar name, 'DWAgHyb21'. 'DWAgHyb21' represents a new perennial grown for landscape and container use.

The new cultivar was derived from a controlled breeding program by the Inventors in Hartebeespoort, North West Province, South Africa. The goal of the breeding program was to develop a new cultivar of *Agapanthus* with resistance to *Erwinia* (soft rot), a reblooming habit, and a compact plant habit with many blooms when grown in a small container. The Inventor made a cross in October of 2018 between unnamed and unpatented proprietary plants of *Agapanthus* from the Inventors' breeding program as both the female and male parents. The Inventors selected 'DWAgHyb21' in July of 2020 as a single unique plant amongst the seedlings that resulted from the above cross.

Asexual propagation of the new cultivar was first accomplished by division by one of the Inventors in Hartebeespoort, North West Province, South Africa in April of 2021. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'DWAgHyb21' as a distinct cultivar of *Agapanthus*.

1. 'DWAgHyb21' exhibits a long flowering period with re-blooming.
2. 'DWAgHyb21' exhibits flowers that are deep purple-blue in color and open from flower buds that are dark purple-blue in color.
3. 'DWAgHyb21' exhibits a very compact plant habit with suitability for use in small containers.
4. 'DWAgHyb21' exhibits a very floriferous blooming habit with a high number of flowering stems.
5. 'DWAgHyb21' exhibits high resistance to crown and root rot.

The female parent of 'DWAgHyb21' differs from 'DWAgHyb21' in having a smaller plant size, less profuse flowering, and less flowers per umbel. The male parent of 'DWAgHyb21' differs from 'DWAgHyb21' in having a larger plant size, flowers that are lighter in color and more flowers per umbel. 'DWAgHyb21' can be most closely compared to the *Agapanthus* cultivars 'ANDBIN' (U.S. Plant Pat. No. 26,336) and 'Charlotte' (not patented). 'ANDBIN' differs from 'DWAgHyb21' in having lighter purple-blue flowers, larger sized leaves, and less inflorescences. 'Charlotte' differs from 'DWAgHyb21' in having flowers that are much lighter in color and leaves that are wider and lighter green in color.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by Concept Plants, Plantipp, and Visions Pictures.

BRIEF DESCRIPTION OF THE DRAWINGS

The accompanying color photographs illustrate the overall appearance and distinct characteristics of the new *Agapanthus*. The photographs were taken of a plant 3 years in age of 'DWAgHyb21' as grown outdoors in a 19-cm container in Lier, Belgium.

The photograph in FIG. 1 provides a side view of a plant of 'DWAgHyb21' in bloom.

Figure 1:
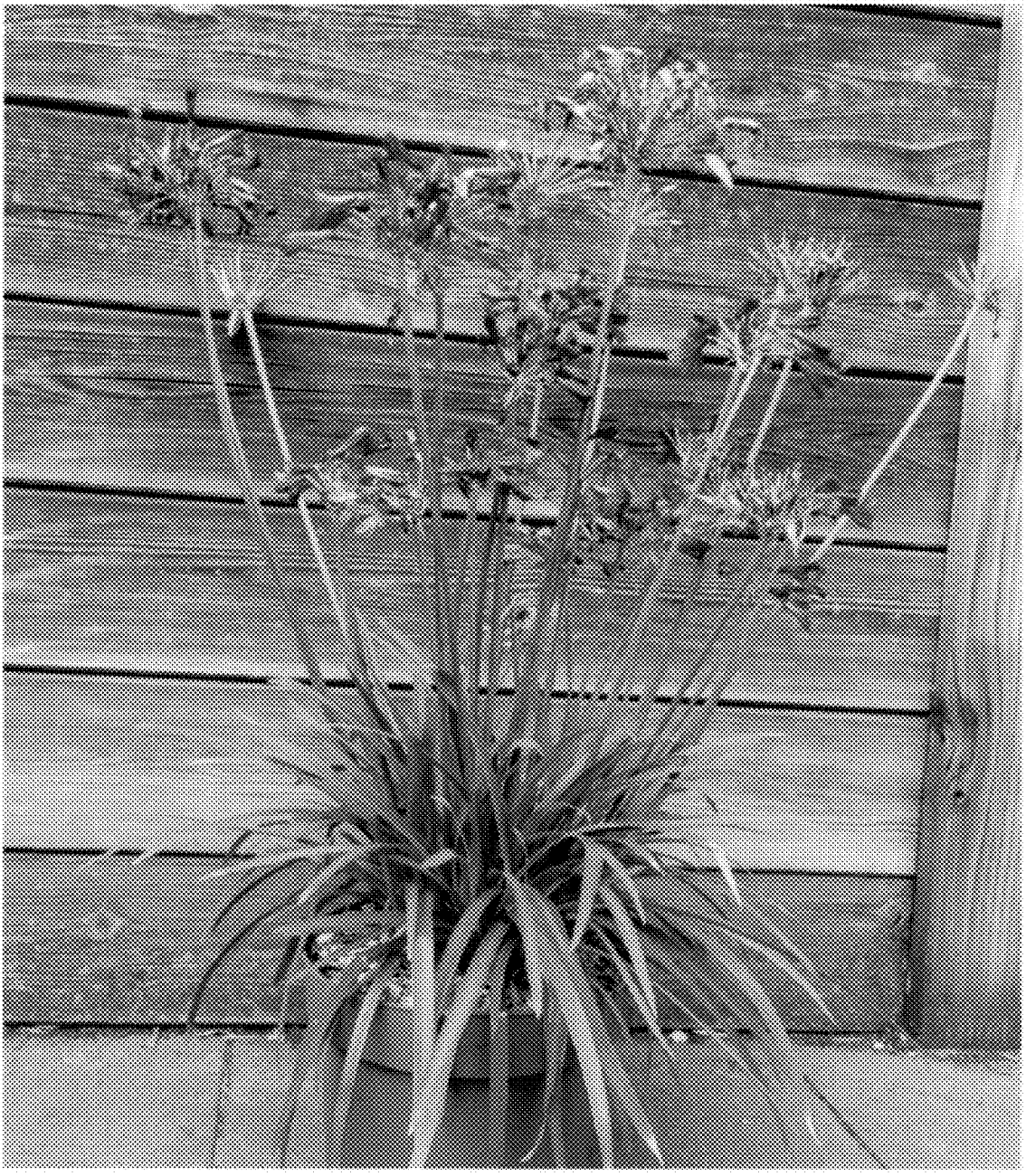
Figure 2:
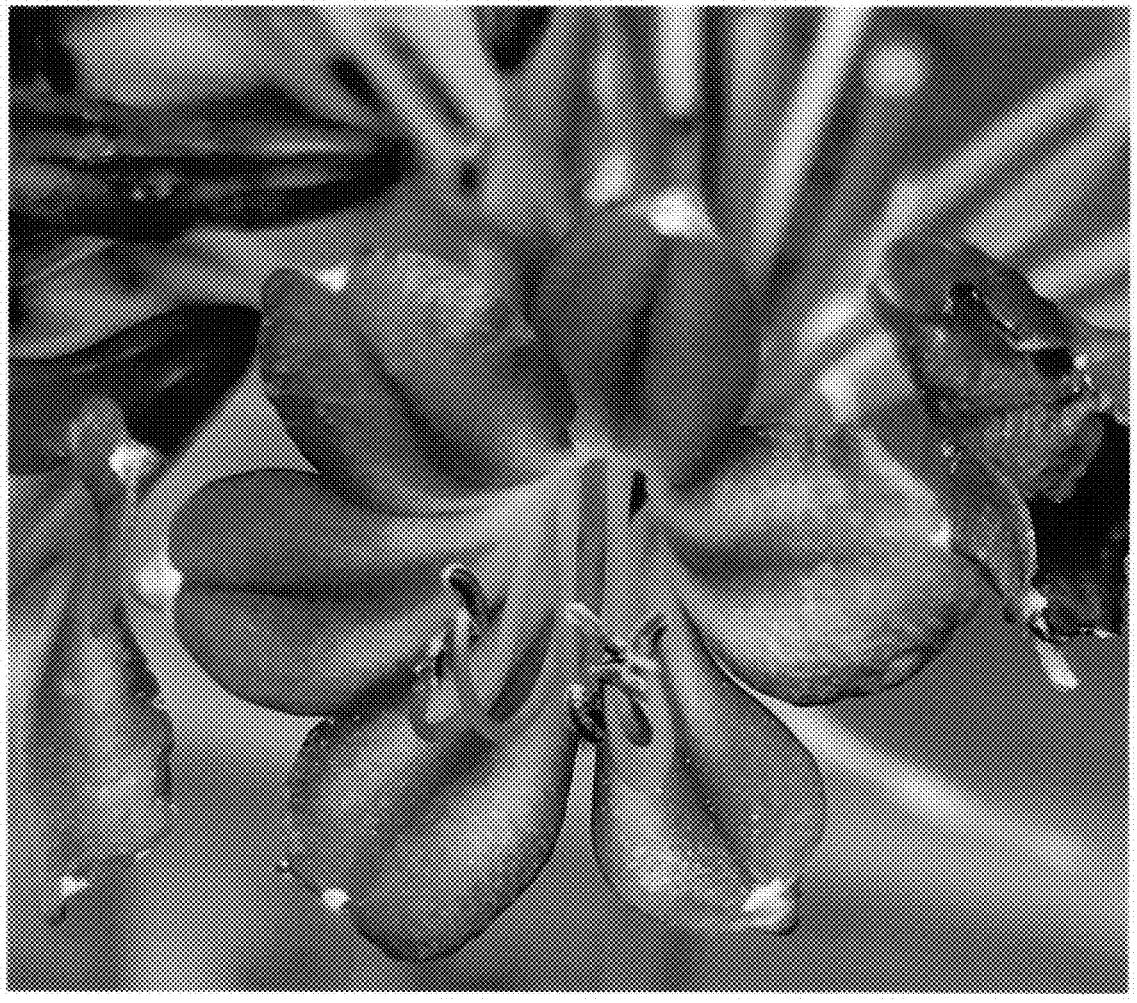

The photograph in FIG. 2 provides a close-up view of an inflorescence of 'DWAgHyb21'.

Figure 3:
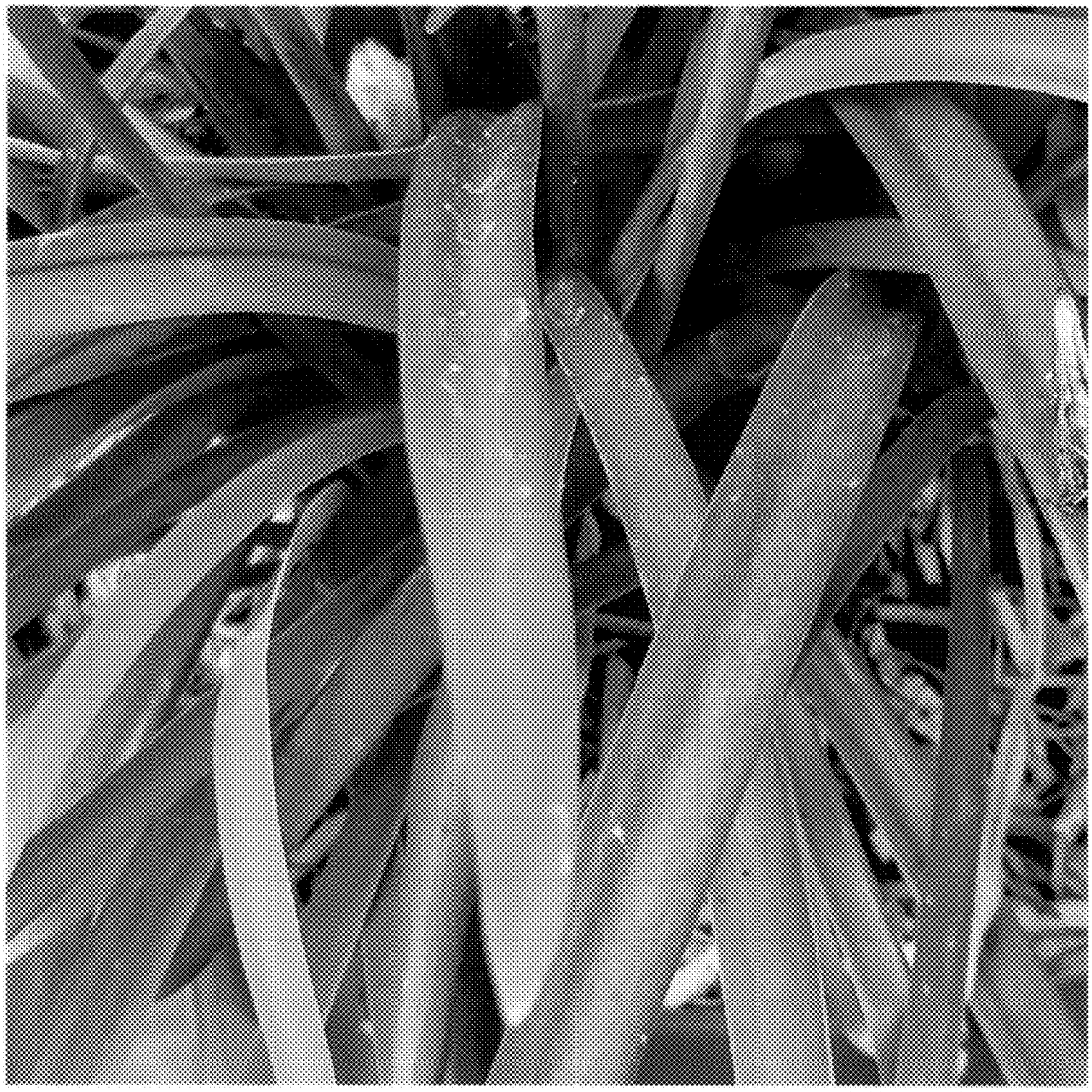

The photograph in FIG. 3 provides a close-up view of the foliage of 'DWAgHyb21'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 3-year-old plants of 'DWAgHyb21' as grown outdoors in 19-cm containers in Boskoop, The Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period*.—June into November, main blooming early to mid-summer with rebloom into November in South Africa.

*Plant type*.—Semi-deciduous (climate dependent) herbaceous perennial, evergreen in South Africa.

*Plant habit*.—Basal rosettes with inflorescences emerging from the rosette center.

*Height and spread*.—46 cm in height and 41 cm in spread as a 3-year-old plant grown in a container.

*Cold hardiness*.—At least to U.S.D.A. Zone 8.

*Diseases and pests*.—Good resistance has been observed to root and crown rot caused by *Erwinia* sp., no resistance or susceptibility to pests has been observed.

*Root description*.—Thick and fleshy.

*Propagation*.—Division and Tissue culture (preferred).

*Growth rate*.—Vigorous.

*Number of shoots* (*rosettes*).—26.

Foliage description:

*Leaf shape*.—Ligulate.

*Leaf division*.—Simple.

*Leaf base*.—Truncate.

*Leaf arrangement*.—2-ranked, arranged in shoots an average of 1.7 cm diameter at base.

*Leaf apex*.—Narrow acute.

*Leaf aspect*. Emerging leaves erect, then cascade.

*Leaf venation*.—Parallel, upper surface; matches surface color, mid-rib upper and lower surface 143B in color.

*Leaf margins*.—Entire.

*Leaf size*.—Up to 18 cm in length and up to 1.1 cm in width.

*Leaf surface*.—Smooth, glabrous, and dull on upper and lower surface.

*Leaf number*.—Average of 32 leaves per rosette.

*Foliage density*.—Medium.

*Leaf color*.—Young and mature upper and lower surfaces 144A, no anthocyanin present.

*Leaf attachment*.—Sessile to base.

Flower description:

*Inflorescence type*.—Dense umbel.

*Flower fragrance*.—None.

*Flower type*.—Rotate, campanulate, base of tepals fused.

*Flower number*.—An average of 20 flowers per umbel.

*Inflorescence size*.—Average of 8 cm in height and 12 cm in diameter.

*Flower size*.—An average of 2.4 cm in depth and 2.3 cm in diameter.

*Lastingness of inflorescence*.—Average 7 days.

*Flower aspect*.—Upright to outward.

*Peduncle*.—1 per rosette, very strong, oval in shape, held primarily upright, surface is satiny, glabrous, slightly glaucous, average of 40 cm in length and 5 mm in width, 144A in color, no anthocyanin present.

*Pedicels*.—Very strong, 3 cm in length and 1 mm in width, held erect to outward, surface is glabrous, color; 144C, top 93A.

*Flower buds*.—Obelliptic in shape, glabrous surface, 2 cm in length, 6 mm in width, color; N89A, young buds 145A.

*Tepals* (*perianth*).—6 lobes, oblanceolate in shape, margins are entire and slightly ruffled, apex is rounded to acute, inner tepals rounded with a slight notch, glabrous and satiny on inner and outer surfaces, thick substance, an average of 2.4 cm in length and 6 mm in width, color; N89C to N89D, central stripe N89A, base NN155A.

*Bracts*.—1, ovate to lanceolate in shape, acuminate apex, truncate base, glabrous and dull surface, 3.2 cm in length, 1.8 cm in width, color; 144B, 93A and 164B.

Reproductive organs:

*Gynoecium*.—Pistil; 1, average of 2.2 cm in length, stigma; narrow clavate in shape, N89D in color, style; 2.2 cm in length, 92A, base N155A, ovary; oblong in shape, 1 cm in length, 4 mm in width and 145C in color, pistillodes not present.

*Androecium*.—Stamens; 6, anthers; dorsifixed, extrusion absent to weak, obcordate in shape, average of 2 mm in length, 202A in color, filament; 2 cm in length, color; 92A, base N155A, pollen; moderate in quantity and 153C in color, staminodes not present.

*Fruit/seed*.—None observed to date.

It is claimed:

1. A new and distinct cultivar of *Agapanthus* plant named 'DWAgHyb21' as herein illustrated and described.

* * * * *